US00PP15446P3

(12) United States Plant Patent
Thomsen

(10) Patent No.: US PP15,446 P3
(45) Date of Patent: Dec. 21, 2004

(54) *EUPHORBIA MILII* PLANT NAMED 'HELENA'

(50) Latin Name: *Euphorbia milii*
Varietal Denomination: Helena

(75) Inventor: Steen Thomsen, Söndersö (DK)

(73) Assignee: Gartneriet Hjortebjerg I/S (DK)

( * ) Notice: Subject to any disclaimer, the term of this patent is extended or adjusted under 35 U.S.C. 154(b) by 0 days.

(21) Appl. No.: 10/762,457

(22) Filed: Jan. 23, 2004

(65) Prior Publication Data

US 2004/0177424 P1 Sep. 9, 2004

(30) Foreign Application Priority Data

Jan. 24, 2003 (QZ) ..... PBR 20030124

(51) Int. Cl.[7] ..... A01H 5/00

(52) U.S. Cl. ..... Plt./302

(58) Field of Search ..... Plt./302

(56) References Cited

PUBLICATIONS

UPOV ROM GTITM Computer database 2004/02 GTI Jove retrieval software.*

* cited by examiner

*Primary Examiner*—Bruce R. Campell
*Assistant Examiner*—W C Haas
(74) *Attorney, Agent, or Firm*—Foley & Lardner, LLP

(57) ABSTRACT

A new distinct cultivar of *Euphorbia milii* plant named 'Helena', particularly characterized by its compact plant habit; very dense and bushy plant form; moderate growth habit; smaller flowers on longer, thinner peduncles; abundant larger floral cymes with white bracts with light green tips; few and small thorns.

2 Drawing Sheets

Genus and species of the plant claimed: *Euphorbia milli* Desmoul.
Variety denomination: 'Helena'.

BACKGROUND OF THE INVENTION

The present invention relates to a new and distinct cultivar of *Euphorbia milii* plant, botanically known as *Euphorbia milii* Desmoul. commonly known as Crown of Thorns, and hereinafter referred to by the name 'Helena'.

The new *Euphorbia milii* is a product of a planned breeding program conducted by Jørgen Nielsen in Haarslev, Fyn, Denmark. The new *Euphorbia milii* originated from a cross made in 2001 by the Inventor, Steen Thomsen. The male parent is an unnamed seedling of *Euphorbia milii* Desmoul. and female parent is an unnamed seedling of *Euphorbia lophogona*. The Inventor selected the new *Euphorbia milii* cultivar from as a single plant the progeny of the above cross in 2001 on the basis of its flower color and compact, freely branching habit. Plants of the new *Euphorbia milii* are upright, compact and have a unique color and abundant small sized flowers.

Asexual reproduction of the new cultivar by terminal cuttings taken and propagated and trial production batches at Hjortebjerg Nurseries, Denmark, has shown that the unique features of this new *Euphorbia milii* are stable and reproduced true to type in many successive generations of asexual reproduction.

BRIEF DESCRIPTION OF THE INVENTION

Plants of the cultivar 'Helena' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'Helena'. These characteristics in combination distinguish 'Helena' as a new and distinct cultivar:

1. White floral bracts 155A, light green tips 145A;
2. Very dense and bushy plant form;
3. Vigorous growth habit; compact plant habit
4. Small flowers on long thin peduncles;
5. Few and small thorns.

Plants of the cultivar 'Helena' can be compared to plants of the cultivar *Euphorbia milii*. 'Themis' (unpatented). Side-by-side comparisons by the Inventor in Haarslev, Denmark, of the cultivar 'Helena' and the cultivar 'Themis' have shown the plants differ in the following characteristics:

1. Plants of the new *Euphorbia milii* have striking white bracts and staminate cyathia with yellow orange glands.
2. Plants of the new *Euphorbia milii* have darker dark green leaves than 'Themis'.
3. Plants of the new *Euphorbia milii* have longer and more upright peduncles than plants of the cultivar 'Themis'.
4. Plants of the new *Euphorbia milii* are smaller than the plants of the cultivar 'Themis'.
5. Plants of the new *Euphorbia milii* have more flowers per plant than the plants of the cultivar 'Themis'.

BRIEF DESCRIPTION OF THE DRAWINGS

The accompanying color photographic drawings illustrate the overall appearance and details of flower form, color and structures of the new cultivar, showing the color as true as it is reasonably possible to obtain in colored reproductions of this type. Colors in the photographs may differ slightly from the color values cited in the detailed description, which more accurately describe the actual colors of the new *Euphorbia milii.*

The first photograph shows a side view of a typical flowering plant of 'Helena', as grown in 11 cm pots.

The second photograph is a close-up of the young and older floral cymes.

DETAILED BOTANICAL DESCRIPTION

In the following description, color references are made to The Royal Horticultural Society Colour Chart, $4^{th}$ edition, where general terms of ordinary dictionary significance are used. Plants were grown under greenhouse conditions. Plants used for this description were grown for about 17 weeks after cutting and produced in 11 cm pots. Other pot sizes can be used and the plants are intended for indoor use or as a bedding plant in temperate climates while it is a perennial garden plant in tropical and subtropical areas.

Botanical classification: *Euphorbia milii* Desmoul. cultivar 'Helena'. *Euphorbiaceae*, Spurge family. Common English name: Crown of Thorns.

Parentage:

*Female parent.*—Unnamed seedling plant of *Euphorbia milii.*

*Male parent.*—Unnamed seedling plant of *Euphorbia milii.*

Type cutting: Terminal vegetative cuttings taken from plants kept in the vegetative stage by shading and high temperatures (25C).

Time to initiate roots: About 10 to 14 days at 18 to 21 C in tunnels in a greenhouse.

Root description: Fine, well branched.

PLANT DESCRIPTION

Form: Perennial plant with upright plant habit. *Euphorbia milii* flowers in cymes with cyathia subtended by colored bracts. Freely branching with about 8 lateral flowering branches froming at every node; dense and bushy. Stems are square to pentagonal with ridges — about 10 mm thick at basis. By each node appear few groups of thorns: 1 large 5 mm and 2–4 smaller 2 mm. Young thorns are green: 145A; while the older ones becomes stiffer and changes color to gray (199C), but most of the thorns disappear before. This cultivar has much fewer thorns than most.

Crop time: After rotting, about 17 weeks required to produce finished flowering plants in 11 cm pots.

Plant height (soil level to top of plant plane): About 14 cm. Width: 15 cm.

Vigor: Vigorous growth rate.

FOLIAGE DESCRIPTION

Leaves alternate, single, obovate shape, margin entire, craspedromous venation. Length: 6 cm. Width: About 24 mm., Apex: acute. Base: cuneate to almost decussate Texture: smooth, waxy, dull., glabrous. Color: Young foliage, upper and lower surfaces: 146D and 147D yellow-green. Mature foliage, upper and lower surfaces: 136A and 147B respectively. Venation, 136A.

FLOWER DESCRIPTION

Flower arrangement and shape: Floral arrangement composed of cymes. The flowers (cyathia) are starky reduced so only a gland and the reproductive organs are present. Subtending the cyathia are two colored bracts. The flowers are further complicated by the unique feature of funnel shaped floral buds appearing at the base of the bracts in two or more layers.

Natural flowering season: Continuous throughout the spring and summer in subtropical and tropical regions. In colder climate season can be extended by greenhouse production with high temperatures and supplementary irradiance.

Flower longevity on the plant: Typically 5–9 weeks; longevity of individual flower is highly dependent on temperature and light conditions. Bracts turn green with age. Entire cymes drop after withering.

Inflorescence size: Diameter approximately 3–6 cm, height: 8 cm.

Flowers: 3 mm diameter, Bracts: overlapping at base, ovoid to inverted cordate, approximately 15 mm in length and 20 mm in width, color from N155D, white with a light green tip (145A) to 155D.

Glands: 5, 5A shiny yellow to 2A yellow-orange during development.

Anthers: Appear after flowers mature; stamen and pollen color 157A, greenish-white.

Pistil and stigma: Appear before cyathia mature; color 1D, greenish-yellow.

Peduncle: Strength: strong. Length: About 5–7 cm. Diameter: About 2 mm. Color: 144C, yellow green at an angle of 30°.

Pedicels: 2 cm long, 2 mm thick strong color: 144C, yellow-green.

Weather tolerance: Plants of the new *Euphorbia milii* have exhibited good tolerance to draught, rain and wind, however flowering may cease during cold and dark periods (<15C).

Pest tolerance: Plants of the new *Euphorbia milii* have exhibited good tolerance to following fungi: Mildew and Thivaliopsis. Also they appear to be less infected by Thrips (Franklinellea).

I claim:

1. A new and distinct cultivar of *Euphorbia milii* plant named 'Helena', as illustrated and described herein.

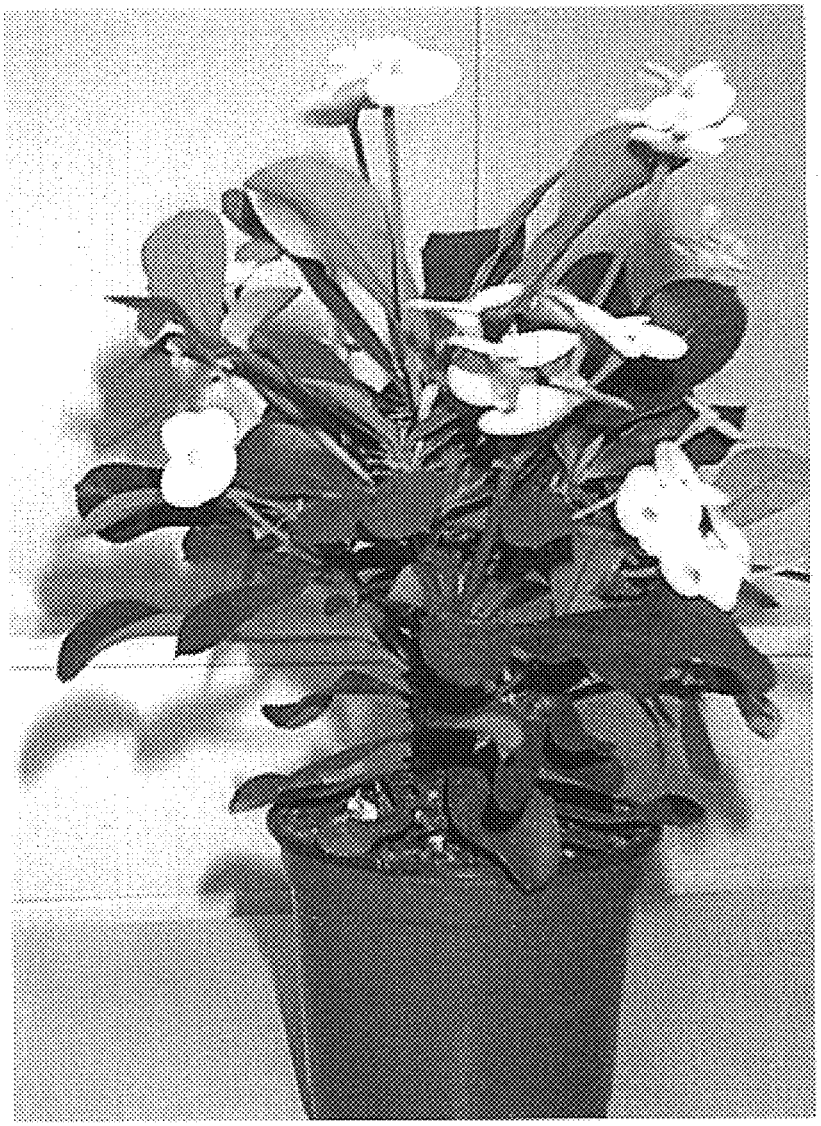

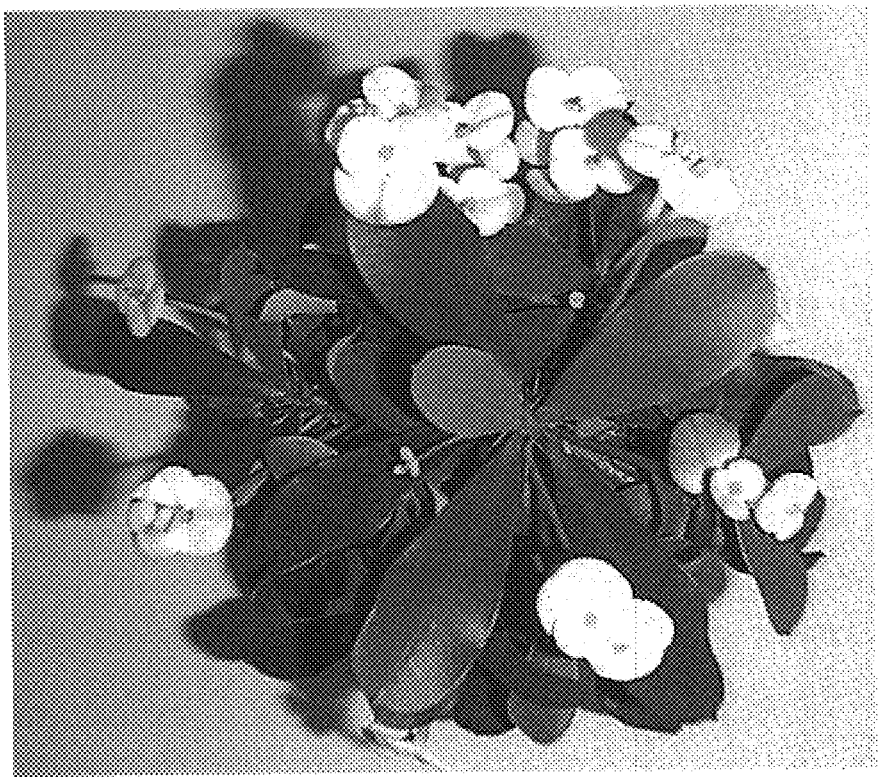

* * * * *